United States Patent [19]

Howat, III

[11] 4,134,795
[45] Jan. 16, 1979

[54] ACETYLENES REMOVAL FROM DIOLEFIN STREAMS BY EXTRACTIVE DISTILLATION

[75] Inventor: Colin S. Howat, III, Prairie Village, Kans.

[73] Assignee: The Goodyear Tire & Rubber Company, Akron, Ohio

[21] Appl. No.: 893,543

[22] Filed: Apr. 5, 1978

[51] Int. Cl.$^2$ .......................... C07C 7/08; B01D 3/40
[52] U.S. Cl. ........................................ 203/53; 203/54; 203/58; 203/60; 203/62; 203/84; 260/681.5 R
[58] Field of Search .................................... 203/50–70, 203/84, 71; 260/681.5 R, 678, 679 A

[56] References Cited

U.S. PATENT DOCUMENTS

| | | | |
|---|---|---|---|
| 3,436,438 | 4/1969 | Takao et al. | 203/60 |
| 3,510,405 | 5/1970 | Takao et al. | 203/60 |
| 3,851,010 | 11/1974 | Rescalli et al. | 260/681.5 R |
| 3,860,496 | 1/1975 | Ginnasi et al. | 260/681.5 R |

*Primary Examiner*—Wilbur L. Bascomb, Jr.
*Attorney, Agent, or Firm*—D. B. Little

[57] ABSTRACT

Acetylenic hydrocarbons are removed from a $C_4$- or $C_5$- hydrocarbon mixture containing a $C_4$- or $C_5$- diolefin respectively. The feedstock (e.g. a $C_4$- or $C_5$- cut from an ethylene plant) is extractively distilled to remove paraffins and mono-olefins in the raffinate, using acetonitrile (ACN), dimethyl formamide (DMF), furfural, acetone, dimethylacetamide or N-methyl-2-pyrrolidone mixed with 0–12 weight percent water as the extraction solvent. The bottoms from this first extractive distillation is subjected to a second extractive distillation in which virtually acetylenes-free solvent is used. Isoprene is withdrawn as the distillate with substantially reduced acetylenes content. The bottoms of the second extractive distillation is split three ways. Two streams are handled conventionally (recycle and heavies removal). The third is stripped free of acetylenes so that it may be used as solvent in the second extractive distillation.

6 Claims, 1 Drawing Figure

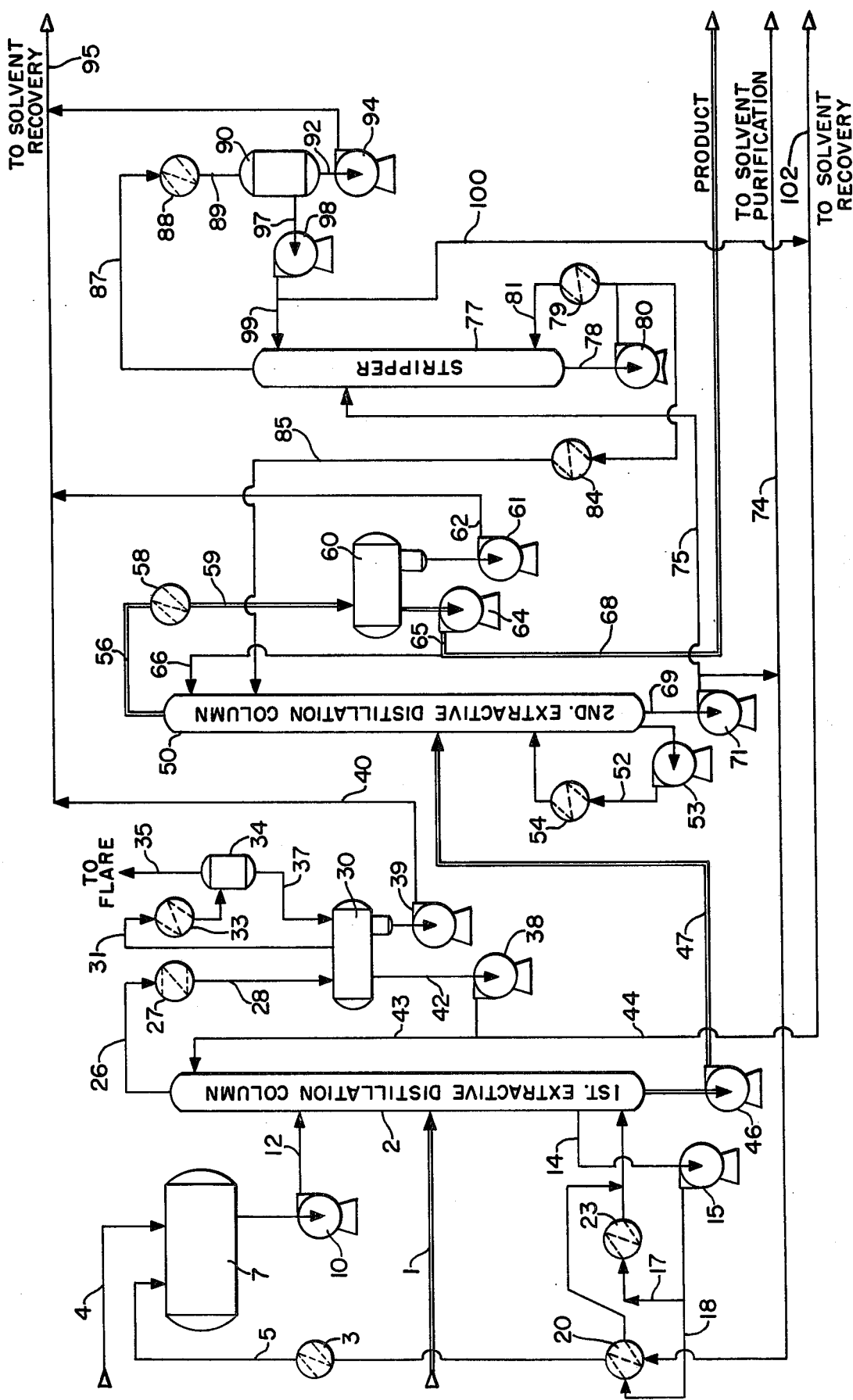

ACETYLENES REMOVAL FROM DIOLEFIN STREAMS BY EXTRACTIVE DISTILLATION

BACKGROUND OF THE INVENTION

The field of this invention is the purification and recovery of diolefins, in particular $C_4$— and $C_5$— diolefins, such as butadiene and isoprene.

In the manufacture of ethylene and/or propylene by the thermal cracking of naphtha, LPG, gas, oil, or fractions thereof, a hydrocarbon fraction containing conjugated diolefins may be obtained. From this fraction may be recovered a $C_4$— fraction comprising 1,3-butadiene, n-butanes, n-butenes, isobutene, vinyl acetylene, ethyl acetylene, 1,2-butadiene, and other $C_4$—'s. A $C_5$— fraction comprising isoprene, 1,3-pentadiene, cyclopentadiene, paraffinic compounds (e.g. isopentane and n-pentane), olefins (e.g. 2-methyl butene-1 and pentene-1), acetylenes (e.g. pentyne-1 and 1-pentene-4-yne), and other hydrocarbons (e.g. benzene, hexane, cyclopentane, cyclopentane and dicyclopentadiene) may also be recovered.

There are numerous patents on the recovery of 1,3-butadiene from the $C_4$— fraction or of isoprene from the $C_5$— fraction, many of which employ extractive distillation using any one of a variety of solvents and a variety of chemical unit operations. Some of the U.S. patents pertinent to this subject matter are:

Nos. 2,407,997 and 2,426,705 — a single extractive distillation and followed by water wash to remove solvent (e.g. acetone) and distillation;

No. 2,437,230 — separating butadiene from butylenes using substantial water with extraction solvent (e.g. 10–55 mole percent);

No. 2,459,403 — two extractive distillations plus an azeotropic distillation;

No. 2,971,036 — single extractive distillation plus cyclopentadiene dimerization and subsequent dimer removal;

No. 3,317,627 — alkynes removed as a side stream after a single extractive distillation;

Other patents pertinent to this field are Nos. 2,993,841; 3,803,258; 3,795,588; 3,655,806; 3,436,437; 3,201,492; and 2,623,844.

In diolefin purification, removal of acetylenic hydrocarbons is of particular importance. Diolefins such as 1,3-butadiene and isoprene are monomer raw materials for the production of synthetic rubber by catalytic solution polymerization. Acetylenes, such as 2-methyl-1-butene-3-yne, inhibit the desired polymerization reaction in concentrations as small as 300 ppm (parts per million). They react with polymerization catalysts, increasing catalyst consumption. For most solution polymerization work, acetylenes should be limited to 100 to 400 ppm maximum concentration, preferably less than 100 ppm.

Several patents have shown the use of extractive distillation processes involving two or more extractive distillations to remove acetylenes from diolefin-containing streams. U.S. Pat. Nos. 3,510,405 and 3,436,438 describe two-stage extractive distillation processes. The first extractive distillation removes paraffins and monoolefins as distillate or raffinate. The extract is stripped so the solvent can be recycled. The stripper distillate is subjected to a second extractive distillation which removes acetylenes as extract. The second extract is stripped in a second stripper to purify the solvent for recycle. Further purification of the isoprene distillate stream from the second extractive distillation is by ordinary distillation. Distillation steps for removal of CPD (cyclopentadiene) may be added according to U.S. Pat. No. 3,510,405.

U.S. Pat. No. 3,784,626 represents another two-stage extractive distillation process similar to 3,510,405 except that both isoprene and dicyclopentadiene leave the process by distillation column side streams, and the extraction solvent is different. Another process which utilizes a two-step extractive distillation and discharges isoprene as a side stream (but in which the isoprene is taken in the raffinate of the first extractive distillation instead of the extract) is described in U.S. Pat. No. 3,851,010.

A three-stage process (i.e. three extractive distillations) is set forth in U.S. Pat. No. 3,860,496. The first extractive distillation (like those of many of the other patents mentioned) removes paraffins and olefins. The second extractive distillation removes cyclopentadiene (CPD) and acetylenes as a side stream, and the third one removes CPD and acetylenes as extract.

The subject of the present invention is a two-stage extractive distillation process which accomplishes the removal of acetylenes from diolefin-containing streams but which utilizes fewer chemical unit operations and a lower extraction solvent flow than processes such as that represented by U.S. Pat. No. 3,436,438, discussed above.

SUMMARY OF THE INVENTION

The present invention is summarized as: a process for the separation of conjugated diolefin from a $C_4$— or $C_5$— hydrocarbon mixture containing said diolefin and acetylenic hydrocarbons which comprises the steps of:

(A) extractively distilling a hydrocarbon feed in a first extractive distillation column;
  (1) in the presence of a solvent selected from the group consisting of acetonitrile (ACN), dimethyl formamide (DMF), furfural, dimethylacetamide, acetone and N-methyl-2-pyrrolidone;
  (2) which solvent contains about 0 to about 12 percent water; and
  (3) withdrawing from the top of said first extractive distillation column a raffinate comprised of olefinic and paraffinic compounds;

(B) extractively distilling the bottoms stream from step (A) in a second extractive distillation column:
  (1) in the presence of a solvent selected from the group consisting of ACN, DMF, furfural, dimethylacetamide, acetone and N-methyl-2-pyrrolidone:
    (a) which solvent contains about 0 to about 12 weight percent water, and
    (b) which solvent is substantially free of acetylenic hydrocarbons; and
  (2) withdrawing from this second extractive distillation column a distillate which contains the conjugated diolefin and substantially lower concentrations of acetylenic hydrocarbons with respect to the conjugated diolefin than did the hydrocarbon feed of step (A);

(C) dividing the bottoms stream from the second extractive distillation of step (B) into three streams;
  (1) the first of which is recycled to step (A),
  (2) the second of which flows to a solvent purification system, and
  (3) the third of which flows to a stripper;

(D) stripping the stream of step (C) (3) in a stripping column and thereby stripping out most of the acetylenic hydrocarbons which are removed in the stripping column distillate; and (E) recycling the stripping column bottoms stream from step (D) to step (B) in which said bottoms stream is the extracting solvent.

In the description which follows from this point on, the explanation of the process will be given mainly with reference to the $C_5-$ fraction, but it is to be understood that the explanation similarly applies to $C_4-$ fractions, i.e. separation of 1,3-butadiene therefrom.

The acetylenic hydrocarbons which are removed by this process are those compounds which have at least one carbon-to-carbon triple bond, e.g. isopropenyl acetylene (or 2-methyl-1-butene-3-yne), pentyne-1, and 1-pentene-4-yne or allyl acetylene.

The presence of a small concentration of water in the extraction solvent enhances the improvement which is achieved in the relative volatilities of the components of the streams being treated by extractive distillation. The concentration of water is limited by its miscibility in the mixture of extraction solvent and hydrocarbons. As water concentration becomes too high, two liquid phases can result, which adversely effects the extractive distillation. At this point foaming many also become a problem. A preferred concentration range for water is 7 to 8 weight percent.

The raffinate from the first extractive distillation column (step A-(3)) is substantially conjugated diolefin-free. In fact, the first extractive distillation performs roughly the same function as it does in most of the other two-stage extractive distillation processes, i.e. removal of monoolefinic and paraffinic hydrocarbons.

However, it is combined with the remaining process steps in a unique way. The second extractive distillation (step B) effectively combines the first stripping column and the second extractive distillation of the older two-stage processes (e.g. U.S. Pat. No. 3,436,438, column 6, line 71-col. 7, line 11) into one unit operation.

In addition, the total amount of extraction solvent necessary for the two extractive distillations has been held to approximately the same amount necessary for a one-stage process through the discovery that only the solvent feed to the second extractive distillation column need be relatively void of acetylenes. Solvent returning to the first extractive distillation may contain acetylenes. Using these discoveries and the fact that a lower flow rate of extraction solvent is needed for the second extractive distillation (because of the lower flow rate of $C_5-$hydrocarbons to be treated) the present process was designed. The lower solvent flow rate to the second extractive distillation results in a higher acetylenes concentration in the extract from that extractive distillation which in turn results in a more efficient solvent stripping operation (step D).

Isoprene with a very low concentration of acetylenes (less than 250 ppm) is taken as the distillate of the second extractive distillation (step B-(2)). It may flow on to further conventional purification steps such as water wash and ordinary distillation.

Essentially, all the solvent, absorbed acetylenes, and some heavy diolefins constitute the bottoms of the second extractive distillation. This stream is divided into three. Two of them (steps C-(1) and (2)) proceed as in a conventional extractive distillation unit. The first may be conveniently recycled to a solvent surge tank for surge as solvent feed to the first extractive distillation.

The second may be sent to a solvent purification unit such as a distillation column for removal of heavy impurities, such as dicyclopentadiene (see U.S. Pat. No. 3,510,405; col. 10, lines 57–65). The third stream is the one sent to the solvent stripper (step D) for acetylene/heavy diolefin removal.

The bottoms from the solvent stripping column (step E) becomes the acetylene-free solvent required for the second extractive distillation (step B). The solvent stripper is operated at a relatively high reflux ratio (e.g. from 140 to 1300:1). However, the distillate rate from this tower is also relatively small due to the small amount of total hydrocarbon being fed to the tower (most of the feed being solvent). Therefore, boil-up rate inside the tower is not prohibitive.

DESCRIPTION OF THE DRAWING

The single FIGURE is a diagrammatic representation of the process of the present invention. It is an exemplary embodiment, and the process is not limited to the arrangement shown. The symbols represent chemical unit operations, and ancillary equipment, such as spare pumps and valves, have not been illustrated. Also, secondary process streams (e.g. vent lines) and utility streams have been omitted.

DESCRIPTION OF THE PREFERRED EMBODIMENTS

Typical hydrocarbon fractions used as feed in diolefin separation processes contain hydrocarbons which are lighter or more volatile than the desired hydrocarbons and some which are heavier or less volatile than the desired hydrocarbons. One or more distillation steps prior to the steps recited in the summary section may be conveniently performed on the crude feed to remove these heavy and light ends of the crude feed stream. This type of operation is shown in U.S. Pat. No. 3,851,010, col. 3, lines 21–26 and U.S. Pat. No. 3,317,627, col. 3, lines 18–20 as being accomplished in a single distillation column. Heavy ends removal is also illustrated by U.S. Pat. Nos. 2,459,403; 2,426,705; and 2,407,997.

The top distillate of the second extractive distillation contains isoprene along with some extraction solvent and water. The water and extraction solvent may be conveniently removed by a water wash or water extraction in which said distillate stream is countercurrently extracted with water. Such a process is illustrated by U.S. Pat. No. 2,426,705, FIG. 1A and column 4, lines 52–60, which is hereby incorporated by reference. Typically, the water wash system is designed to reduce the solvent concentration in the stream to less than 10 ppm.

The washed isoprene-containing stream may yet contain compounds other than isoprene which would adversely effect polymerization. These impurities may be small amounts of hydrocarbons having a different number of carbon atoms than the desired isoprene, and they can also include compounds having the same number of carbon atoms as the desired conjugated diolefin, but whose boiling points are somewhat different from that of the desired diolefin (e.g. 1,3-pentadienes, cyclopentadiene). These types of impurities can be removed by standard distillation techniques. Such processes are illustrated by the following U.S. Pat. Nos.: 2,426,705, FIG. 1A and col. 4, lines 60–71 (which illustrates the removal of heavy impurities); 3,510,405, col. 10, lines 32–56 (which illustrates the removal of light impurities); and 3,436,438, col. 6, lines 9–15. This distillation step is called the isoprene refining step. After the removal of heavy acetylenes (e.g. pentyne-1) in this step, total acetylenes concentration is less than 100 ppm.

In the case of isoprene, one of the more important impurities which is removed by isoprene refining is cyclopentadiene which exits in the bottoms of the isoprene refining step. There are other ways to remove cyclopentadiene, as discussed in the background section, but whatever the technique used, it should be reduced to below several ppm concentration in the product isoprene.

For purposes of this application, the term "ppm or parts per million with respect to isoprene (or conjugated diolefin)" means the weight of the measured compound in the stream divided by the weight of isoprene in the stream, which quotient is multiplied by one million.

As an aid in understanding the process of this invention, the overall process will be described with reference to the flow diagram. Throughout this detailed description, process parameters (e.g. stream compositions, temperatures, pressures, and equipment description) will be given. These process parameters are to be considered exemplary only and not limitative as to the scope of this invention.

The hydrocarbon feed stream 1 enters the first extractive distillation column 2 at a point in between the points of withdrawal for the distillate and bottoms. Stream 1 is normally a liquid, a typical example of which is given in Table 1.

Table 1

| Feed Stream 1 Typical Composition | | |
|---|---|---|
| Component | Mole Percent | Weight % or ppm |
| Nitrogen | 0.231 | 932.3 ppm |
| 1,4PD (1,4-Pentadiene) | 0.093 | 920.9 ppm |
| 1-Pentane | 2.918 | 3.033 |
| Isopropenyl Acetylene | 0.000 | 5.0 ppm |
| Pentene-1 | 6.345 | 6.410 |
| 2MB1 (2-methyl-1-butene) | 9.447 | 9.545 |
| Isoprene | 35.407 | 34.746 |
| 1Pen4yne (1-pentene-4-yne) | 0.032 | 304.6 ppm |
| N-Pentane | 18.884 | 19.627 |
| Pentyne-1 | 0.094 | 926.1 ppm |
| T-Pente2 (trans-2-pentene) | 5.889 | 5.950 |
| C-Pente2 (cis-2-pentene) | 2.895 | 2.925 |
| 2MB2 (2-methyl-2-butene) | 3.750 | 3.789 |
| CPD (cyclopentadiene) | 3.163 | 3.012 |
| T-PIP (trans-piperylene) | 6.410 | 6.289 |
| C-PIP (cis-piperylene) | 2.985 | 2.929 |
| Cyclopentene | 1.239 | 1.216 |
| Cyclopentane | 0.218 | 0.220 |
| Total | 100.000 | 100.000 |
| Total Mols/hr. = 937.7 | | |
| Temp. Deg. C. 63 | | |
| Pressure, kPa (KiloPascals) | 723 | |

The extraction solvent 12 (preferably acetonitrile) is supplied from solvent surge tank 7 via pump 10. Said surge tank is supplied with fresh solvent 4 and recycled solvent 5, and is blanketed with nitrogen to prevent oxygen from entering the system.

The first extractive distillation column typically has 72 trays. The feed is on the 36th tray from the top, and the solvent enters on the 10th tray. A typical operating pressure for the column is 20 psig. (138 kPa).

The bottom of the column is heated by reboiler 23 and solvent exchanger 20. Reboiler pump 15 circulates a stream 14 from the bottom of the column through the two heat exchangers. Solvent exchanger 20 conserves heat by transferring heat from recycle stream 5 to stream 18 (part of circulating stream 14). Recycle solvent 5 must be cooled prior to storage in the solvent surge tank 7, and it is further cooled after solvent exchanger 20 with cooling water in recycle solvent cooler 3. Further savings in steam (the heating medium for reboiler 23) may be realized by transferring heat to another part of circulating stream 14 from other streams with excess heat content (e.g. condensers in the solvent recovery area of the plant).

The first extractive distillation overhead vapors 26 are condensed in condenser 27, and condensed stream 28 flows to overhead drum 30. Reflux pump 38 withdraws stream 42 from the reflux drum and said stream is split on the discharge side of said pump into reflux stream 43 and raffinate 44 (principally monoolefins and paraffins). Any water/solvent mixture which collects as a separate phase in the boot or sump part of reflux drum 30 is withdrawn by water phase pump 39 as stream 40. The vapors which exist in reflux drum 30 flow through pipe 31 through vent chiller 33 which removes heat from stream 31 by transferring it to a refrigerant such as propane. After being chilled, stream 31 flows into disengaging drum 34 wherein the noncondensables 35 are sent to a flare and the condensed materials 37 are returned to reflux drum 30.

Reflux ratio, for purposes of this application expressed as $R_D$, is the ratio of moles per hour reflux to moles per hour distillate (or raffinate in the case of extractive distillation). Reflux ratio for the first extractive distillation is typically in the range of about 3 to 6.

The isoprene-laden solvent stream (or extract) stream 47 is transferred to the second extractive distillation column 50 by bottoms pump 46. This stream contains essentially all the acetylenes, all the heavy diolefins, 99% of the isoprene, and some heavy olefins. In addition, it contains essentially all the solvent fed to the first extractive distillation column.

At the conditions stated, an extract 47 and a raffinate 44 having the composition shown in Table 2 are obtained:

Table 2

| | Stream 44 Raffinate | | Stream 47 Extract | |
|---|---|---|---|---|
| Compnent | Mole Per- cent | Weight % or ppm | Mole Per- cent | Weight % or ppm |
| 1,4PD | 0.030 | 313.4 ppm | 0.008 | 139.1 ppm |
| 1-Pentane | 4.926 | 5.378 | 0.000 | 0.000 |
| Isoprepenyl Acetylene | 0.000 | 0.000 | 0.000 | 1.9 ppm |
| Pentene-1 | 10.708 | 11.362 | 0.000 | 4.8 ppm |
| 2MB1 | 15.884 | 16.855 | 0.004 | 76.4 ppm |
| Isoprene | 0.516 | 0.532 | 3.716 | 6.465 |
| 1Pen4yne | 0.002 | 24.6 ppm | 0.010 | 171.7 ppm |
| N-Pentane | 31.899 | 34.821 | 0.000 | 0.000 |
| Pentyne-1 | 0.009 | 94.8 ppm | 0.028 | 491.6 ppm |
| T-Pente2 | 9.900 | 10.505 | 0.003 | 55.0 ppm |
| C-Pente2 | 4.846 | 5.142 | 0.002 | 50.2 ppm |
| 2MB2 | 5.454 | 5.787 | 0.055 | 988.5 ppm |
| CPD | 0.015 | 159.4 ppm | 0.322 | 0.544 |
| T-PIP | 0.089 | 921.6 ppm | 0.714 | 1.243 |
| C-PIP | 0.084 | 867.4 ppm | 0.399 | 0.695 |
| Cyclopentene | 0.007 | 79.6 ppm | 0.130 | 0.226 |
| Cyclopentane | 0.000 | 3.4 ppm | 0.023 | 413.3 ppm |
| Dicyclopentadiene | 0.000 | 0.000 | 0.146 | 0.493 |
| ACN | 14.666 | 9.110 | 76.267 | 83.113 |
| Water | 0.964 | 0.262 | 15.173 | 6.982 |
| Total | 100.000 | 100.000 | 100.000 | 100.000 |
| Total Moles/hr. | 608.3 | | 8875.2 | |
| Temp. Deg. C. | 46.7 | | 99.4 | |
| Pressure, PSIA | 123.000 (847.5 kPa) | | 98.000 (675.2 kPa) | |

Stream 47 enters column 50, 31 trays down from the top of the tower which typically has 64 trays.

Column 50 typically operates at about 18 psig (124 kPa) at the top and a bottoms temperature of about 112° C.

The relative volatility adjustment, which allows the separation between isoprene and acetylene, requires the presence of solvent 85 on the separating trays above the feed as well as below. Therefore, extraction solvent must be fed high in the tower in a similar manner to any other conventional extractive distillation step. However, this solvent must be acetylenes free; otherwise, acetylenes contained in the solvent would contaminate the product. Solvent 85 from the bottom of stripper 77 is fed to tray 10 of column 50. The top 9 trays of column 50 are for solvent disengagement. Of the total solvent circulation in this process, approximately 70% is fed to the first extractive distillation 2, and approximately 30% is fed separately to column 50.

The purpose of the second extractive distillation is to reduce acetylenes concentration in the isoprene-containing product to an acceptably low level. The design in this particular instance, is to reduce 1-pentene-4-yne to a level less than 100 ppm with respect to isoprene. However, this operation also reduces the amount of other acetylenes present in the feed to this tower (isopropenyl acetylene and pentyne-1 by 70 and 96%, respectively, based on amount of these in feed stream 47). This separation is affected with a reflux ratio ($R_D$) generally in the range of about 4/1 to 11/1.

Heat is furnished to the second extractive distillation column by circulating stream 52 from the bottom of said column via bottoms pump 53 through reboiler 54 (steam heated) and back into the bottom of the column.

The distillate vapors 56 are condensed in condenser 58, and the condensed stream 59 flows into reflux drum 60. A stream of the condensed overheads 65 is withdrawn from the reflux drum by overhead pump 64, and this stream is split into two streams, a reflux stream 66 and product or distillate stream 68. The product stream contains: nearly all the isoprene fed to the process, most of the heavy diolefins fed to the process (e.g. piperylenes), and acetylenes (reduced to within the desired concentration limits with respect to isoprene). It has been found that a spray of liquid down onto the tubes of condenser 58 is helpful in inhibiting bacteria growth on the tubes. The spray stream may be a small flow taken from stream 66 and sent to the top of condenser 58.

Any of the acetonitrile (ACN)/water extraction solvent which carries over into the reflux drum 60 and separates as a lower liquid phase in the boot or sump section of said drum is withdrawn as an aqueous phase 62 by water phase pump 61.

The remaining diolefins and almost all of the acetylenes incoming to the process appear in the bottoms 69 of the second extractive distillation with the extraction solvent.

Typical compositions for streams 68 and 69 are given in Table 3.

Table 3

| Component | Bottoms Stream 69 | | Stream 68-Distillate Product | |
|---|---|---|---|---|
| | Mole Percent | Weight % or ppm | Mole Percent | Weight % or ppm |
| 1,4PD | 0.000 | 0.000 | 0.143 | 0.148 |
| Isopropenyl acetylene | 0.000 | 1.0 ppm | 0.000 | 6.1 ppm |
| Pentene-1 | 0.000 | 0.000 | 0.004 | 51.8 ppm |
| 2MB1 | 0.000 | 0.000 | 0.076 | 818.7 ppm |
| Isoprene | 0.008 | 152.0 ppm | 66.562 | 68.994 |
| 1Pen4yne | 0.007 | 130.4 ppm | 0.003 | 32.5 ppm |
| Pentyn-1 | 0.020 | 364.5 ppm | 0.018 | 186.7 ppm |
| T-Pente 2 | 0.000 | 0.000 | 0.055 | 589.7 ppm |
| C-Pente 2 | 0.000 | 0.000 | 0.050 | 537.9 ppm |
| 2MB2 | 0.000 | 0.000 | 0.991 | 1.058 |
| CPD | 0.006 | 116.4 ppm | 5.633 | 5.666 |

Table 3-continued

| Component | Bottoms Stream 69 | | Stream 68-Distillate Product | |
|---|---|---|---|---|
| | Mole Percent | Weight % or ppm | Mole Percent | Weight % or ppm |
| T-PIP | 0.046 | 833.4 ppm | 11.722 | 12.150 |
| C-PIP | 0.096 | 0.173 | 4.854 | 5.032 |
| Cyclopentene | 0.000 | 0.000 | 2.343 | 2.429 |
| Cyclopentane | 0.000 | 0.000 | 0.414 | 0.442 |
| DCPD | 0.156 | 0.547 | 0.000 | 0.000 |
| ACN | 84.458 | 91.863 | 5.431 | 3.393 |
| Water | 15.203 | 7.257 | 1.701 | 0.466 |
| Total | 100.000 | 100.000 | 100.000 | 100.000 |
| Total Moles/hr. flow | 11,974.2 | | 494.0 | |
| Temp. Deg. C | 112 | | 57 | |
| Pressure, kPa | 785 | | 841 | |

Bottoms stream 69 is withdrawn by bottoms pump 71 and splits into three streams on the discharge side of said pump. Approximately 67% of the bottoms flows as stream 5 to solvent exchanger 20. About 2 percent of the bottoms, as stream 74, flows to solvent purification, which (as discussed previously) may be a distillation which removes impurities such as dicyclopentadiene (DCPD) from the solvent as a bottoms stream. The distillate from said distillation is then recycled to the solvent surge tank 7. Both this distillate and the recycle stream 5 are comprised of ACN and water; however, they contain small amounts of impurities, such as 1,3-pentadienes. These contaminants are acceptable for the solvent to be recycled to the first extractive distillation, but not for that to be used in the second extractive distillation.

The remainder of the bottoms (stream 75) is fed to the stripper 77 for removal of acetylenes and heavy diolefin. In the stripper, all of the isopropenyl acetylene and pentyne-1 plus 98 percent of the 1-pentene-4-yne in stream 75 are removed from the solvent by taking them overhead in the distillate. The overheads vapors 87 are condensed in condenser 88, and the condensed stream 89 flows into overheads drum 90. Stripper reflux pump 98 withdraws a stream 97 comprised of ACN, water, heavy diolefins, and acetylenes. This stream is split into two streams, one of which is the reflux 99 to the stripper, and the other (distillate stream 100) is added to the raffinate 44 from the first extractive distillation. A typical composition for stream 100 is given in Table 4.

Table 4

| Component | Distillate Stream 100 | |
|---|---|---|
| | Mole Percent | Weight % or ppm |
| Isopropenyl Acetylene | 0.025 | 265.4 ppm |
| Isoprene | 3.887 | 4.254 |
| 1Pen4yne | 3.375 | 3.584 |
| Pentyn-1 | 9.312 | 10.191 |
| CPD | 3.062 | 3.252 |
| T-PIP | 21.287 | 23.296 |
| C-PIP | 44.262 | 48.439 |
| ACN | 7.225 | 4.765 |
| Water | 7.562 | 2.189 |
| Total | 100.000 | 100.000 |
| Temp. Deg. C. 58 | | |
| Pressure, PSIA (kPa) 146.0 (1006) | | |

The combined stream 102 is sent to a process for solvent recovery. Such a process may consist of a water wash or water extraction to remove the ACN and water as extract. The organic raffinate from said water wash would then contain paraffins, olefins, acetylenes, and other impurities and could be disposed of. The aqueous extract can subsequently be distilled to recover the solvent as distillate which then could be recycled to the solvent surge tank 7. Such a system (designed, however, for DCPD removal) is described in U.S. Pat. No. 2,426,705 at FIG. 1A, col. 4, line 73 -col. 5, line 7 and col. 9, line 53 to col. 10, line 50.

Again, any ACN/water phase which may collect in the bottom of the stripper overhead drum is withdrawn as stream 92 by stripper water phase pump 94. The three water phase streams (40, 62 and 92) are combined into stream 95 which is sent to a solvent recovery system (e.g. a distillation for separation of water from said stream which may thereafter be recycled to solvent surge tank 7).

Stripper 77 is typically a 74 tray tower with the feed on the 12th tray counting from the top, at a pressure of about 15 psig (103 kPa), and about 111° C. bottom temperature. Under these conditions a nearly acetylene-free solvent stream is obtained as the bottoms 78. This bottoms stream is withdrawn from the stripper by stripper bottoms pump 80. Part of it, 81, is circulated through stripper reboiler 79 and returned to the bottom of the stripper in order to furnish heat to the stripper. The extraction solvent for the second extractive distillation 85 flows from the discharge of pump 80 through stripper solvent cooler 84 which lowers the temperature of said stream to approximately that of the tenth tray of column 50 (e.g. 66° C.). A bypass pipe around stripper solvent cooler 84 with a control valve (controlled by a temperature controller on the discharge side of the solvent cooler) is a preferred method for adjusting flow through the solvent cooler and thereby controlling the temperature of stream 85.

The difference between the quality of the extraction solvent used for column 2 and that for column 50 is made clearer by Table 5 which shows typical compositions for the streams.

Table 5

| | Typical Compositions | | | |
|---|---|---|---|---|
| | Stream Number 12 Solvent Feed to Column 2 | | Stream Number 85 Solvent Feed to Column 50 | |
| Component | Mole Percent | Weight % or ppm | Mole Percent | Weight % or ppm |
| Nitrogen | 0.000 | 2.0 ppm | 0.000 | 0.000 |
| 1,4PD | 0.000 | 3.3 ppm | 0.000 | 0.000 |
| 1-Pentane | 0.030 | 590.3 ppm | 0.000 | 0.000 |
| Isopropenyl Acetylene | 0.000 | 1.0 ppm | 0.000 | 0.000 |
| Pentene-1 | 0.067 | 0.124 | 0.000 | 0.000 |
| 2MB1 | 0.099 | 0.185 | 0.000 | 0.000 |
| Isoprene | 0.011 | 205.1 ppm | 0.000 | 0.000 |
| 1Pen4yne | 0.007 | 126.0 ppm | 0.000 | 2.3 ppm |
| N-Pentane | 0.199 | 0.382 | 0.000 | 0.000 |
| Pentyne-1 | 0.019 | 325.8 ppm | 0.000 | 0.000 |
| T-Pente2 | 0.061 | 0.115 | 0.000 | 0.000 |
| C-Pente2 | 0.030 | 564.5 pm | 0.000 | 0.000 |
| 2MB2 | 0.034 | 635.3 ppm | 0.000 | 0.000 |
| CPD | 0.006 | 114.2 ppm | 0.000 | 0.000 |
| T-PIP | 0.045 | 814.4 ppm | 0.000 | 0.000 |
| C-PIP | 0.092 | 0.168 | 0.000 | 0.000 |
| Cyclopentene | 0.000 | 0.8 ppm | 0.000 | 0.000 |
| DCPD | 0.141 | 0.498 | 0.157 | 0.550 |
| ACN | 82.910 | 90.413 | 84.867 | 92.302 |
| Water | 16.249 | 7.777 | 14.976 | 7.148 |
| Total | 100.000 | 100.000 | 100.000 | 100.000 |
| Total Moles/ hr. flow = | 8609 | | 3668 | |

Except where otherwise stated, heat exchangers used to cool process fluids such as condensors in this process may utilize plant cooling water (typically 32° C.) as the cooling medium and heat exchangers used for heating such as reboilers utilize steam as the heating medium (typically saturated steam at 156° C.).

Other embodiments of this invention will be apparent to those skilled in the art from a consideration of this specification or practice of the invention disclosed herein. It is intended that the specification, drawing, and detailed description be considered as exemplary only, with the true scope and spirit of the invention being indicated by the following claims.

What is claimed is:

1. A process for the separation of a conjugated diolefin from a $C_4-$ or $C_5-$ hydrocarbon mixture containing said diolefin and acetylenic hydrocarbons which comprises the steps of:
    (A) extractively distilling a hydrocarbon feed in a first extractive distillation column:
        (1) in the presence of a solvent selected from the group consisting of acetonitrile (ACN), dimethyl formamide (DMF), furfural, acetone, dimethylacetamide and N-methyl-2-pyrrolidone;
        (2) which solvent contains about 0 to about 12 weight percent water; and
        (3) withdrawing from the top of said first extractive distillation column a raffinate comprised of olefinic and paraffinic compounds;
    (B) extractively distilling the bottoms stream from step (A) in a second extractive distillation column:
        (1) in the presence of a solvent selected from the group consisting of ACN, DMF, furfural, acetone, dimethylacetamide, and N-methyl-2-pyrrolidone:
            (a) which solvent contains about 0 to about 12 weight percent water, and
            (b) which solvent is substantially free of acetylenic hydrocarbons; and
        (2) withdrawing from this second extractive distillation column a distillate which contains the conjugated diolefin and substantially lower concentrations of acetylenic hydrocarbons with respect to the conjugated diolefin than did the hydrocarbon feed of step (A):
    (C) dividing the bottoms stream from the second extractive distillation of step (B) into three streams:
        (1) the first of which is recycled to step (A),
        (2) the second of which flows to a solvent purification system, and
        (3) the third of which flows to a stripper;
    (D) stripping the stream of step (C) (3) in a stripping column and thereby stripping out most of the acetylenic hydrocarbons which are removed in the stripping column distillate; and
    (E) recycling the stripping column bottoms stream from step (D) to step (B) in which said bottoms stream is the extracting solvent.

2. The process as recited in claim 1 wherein the conjugated diolefin is 1,3-butadiene.

3. The process as recited in claim 1 wherein the conjugated diolefin is isoprene.

4. The process as recited in claim 3 wherein the solvent of steps A and B is acetonitrile.

5. The process as recited in claim 4 wherein the distillate stream of step B-2 contains less than 250 ppm. total acetylenic hydrocarbons.

6. The process as recited in claim 5 wherein the specific acetylenic hydrocarbons removed are 1 -pentene-4-yne, isopropenyl acetylene and pentyne-1.

* * * * *